United States Patent
Kuster et al.

(10) Patent No.: US 10,545,326 B2
(45) Date of Patent: *Jan. 28, 2020

(54) ILLUMINATION AND OBSERVATION SYSTEM FOR AN OPHTHALMIC MICROSCOPE, OPHTHALMIC MICROSCOPE AND MICROSCOPYING METHOD USING FOUR RED REFLEX OBSERVATION PUPILS

(71) Applicant: LEICA INSTRUMENTS (SINGAPORE) PTE. LTD., Singapore (SG)

(72) Inventors: Manfred Kuster, Widnau (CH); Michael Guentert, Heerbrugg (CH)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 15/750,192

(22) PCT Filed: Aug. 23, 2016

(86) PCT No.: PCT/SG2016/000012
§ 371 (c)(1),
(2) Date: Feb. 4, 2018

(87) PCT Pub. No.: WO2017/034474
PCT Pub. Date: Mar. 2, 2017

(65) Prior Publication Data
US 2018/0224647 A1    Aug. 9, 2018

(30) Foreign Application Priority Data
Aug. 24, 2015    (EP) .................................... 15182106

(51) Int. Cl.
*A61B 3/13*    (2006.01)
*G02B 21/00*    (2006.01)
(Continued)

(52) U.S. Cl.
CPC .............. *G02B 21/22* (2013.01); *A61B 3/132* (2013.01); *G02B 21/0012* (2013.01); *G02B 21/082* (2013.01)

(58) Field of Classification Search
None
See application file for complete search history.

(56) References Cited

U.S. PATENT DOCUMENTS 5,760,952 A * 6/1998 Koetke ................ G02B 21/082
351/205
5,856,883 A * 1/1999 Sander ................ G02B 21/082
359/389

(Continued)

FOREIGN PATENT DOCUMENTS

DE    102009028229 B3    12/2010
EP    0661020 B1    5/2001
EP    1341024 A1    9/2003
EP    1455215 A2    9/2004

*Primary Examiner* — Derek S. Chapel
(74) *Attorney, Agent, or Firm* — Hodgson Russ LLP

(57) ABSTRACT

An illumination and observation system (1) for an ophthalmic surgical microscope (2) has first, second, third and fourth observation pupils (4, 5, 8, 9) for two observers, a coaxial illumination (6, 10, 11) in the first, third and fourth observation pupils to generate a red reflex (13) therein, and a main illumination (7) in the second observation pupil. For widely illuminating the surroundings, the main illumination has a larger illumination field than the coaxial illumination in any of the first, third and fourth observation pupils. For superior observation quality and a visible and homogenous red reflex in the second observation pupil, the main illumination overlaps at least 50% with the second observation pupil. The main illumination may be aligned within ±5° to (Continued)

an optical axis (12) of the second observation pupil and to overlap the coaxial illumination at least 50% with the first, third and fourth observation pupils.

14 Claims, 3 Drawing Sheets

(51) Int. Cl.
*G02B 21/08* (2006.01)
*G02B 21/22* (2006.01)

(56) References Cited

U.S. PATENT DOCUMENTS

| | | | | |
|---|---|---|---|---|
| 6,011,647 | A * | 1/2000 | Geschwentner | A61B 3/132 351/216 |
| 8,523,359 | B2 * | 9/2013 | Merz | A61B 3/12 351/200 |
| 8,941,915 | B2 * | 1/2015 | Kuster | G02B 21/0012 359/376 |
| 2004/0227989 | A1 * | 11/2004 | Obrebski | G02B 21/0012 359/388 |
| 2008/0297892 | A1 * | 12/2008 | Abele | A61B 3/13 359/389 |
| 2014/0029089 | A1 * | 1/2014 | Guentert | G02B 21/22 359/377 |
| 2014/0152959 | A1 | 6/2014 | Kuster et al. | |
| 2018/0231757 | A1 * | 8/2018 | Kuster | A61B 3/132 |

\* cited by examiner

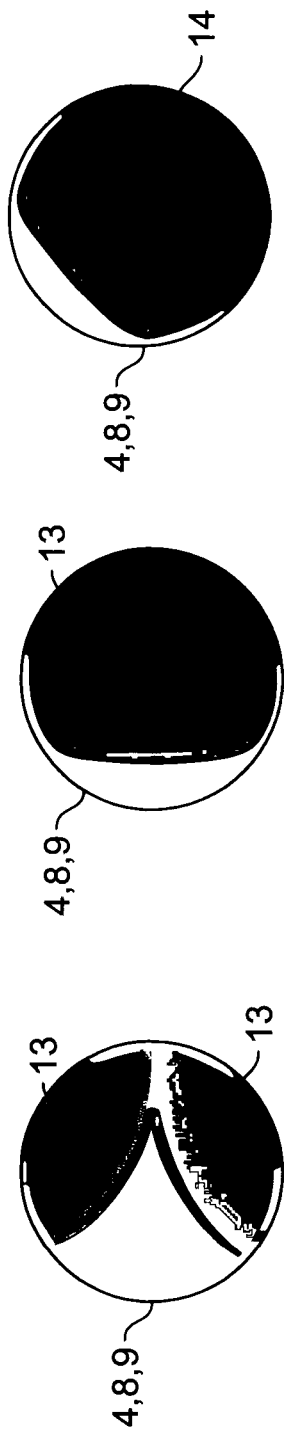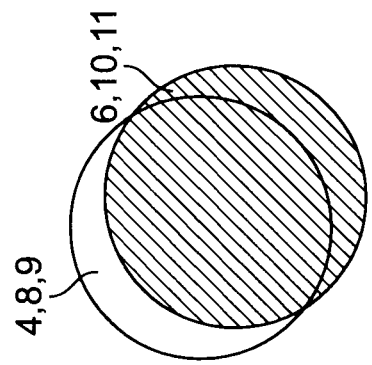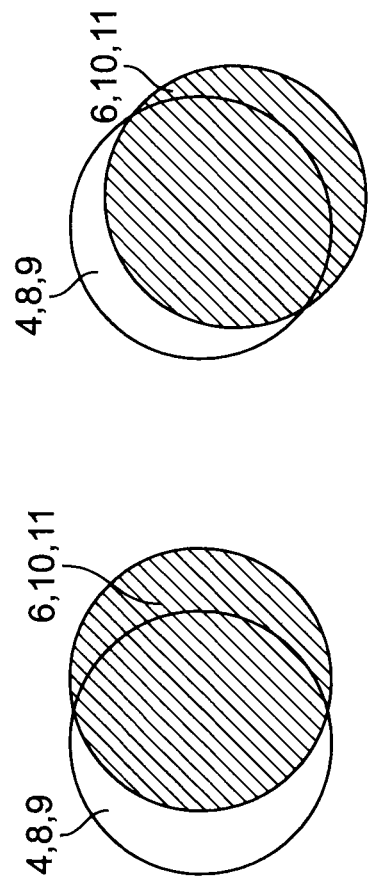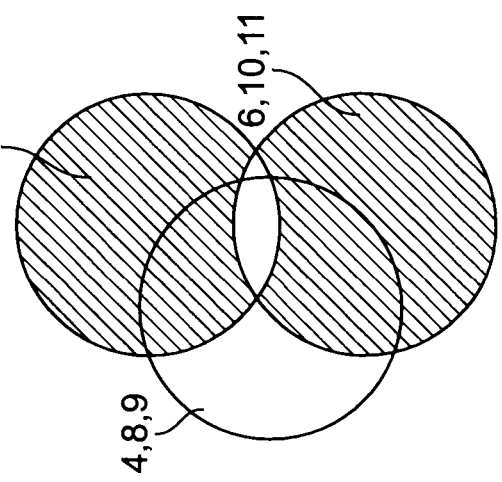

ILLUMINATION AND OBSERVATION SYSTEM FOR AN OPHTHALMIC MICROSCOPE, OPHTHALMIC MICROSCOPE AND MICROSCOPYING METHOD USING FOUR RED REFLEX OBSERVATION PUPILS

CROSS-REFERENCE TO RELATED APPLICATIONS

The present application is the U.S. national phase of International Application No. PCT/SG2016/000012 filed Aug. 23, 2016, which claims priority of European Application No. 15182106.3 filed Aug. 24, 2015, the entire disclosure of which is incorporated herein by reference.

FIELD OF THE INVENTION

The invention relates to an illumination and observation system for a microscope, in particular a microscope for performing eye surgery on an observed eye, the system comprising a first, second, third and fourth observation pupil for the eyes of two observers such as a surgeon and an assistant, a coaxial illumination in the first, third and fourth observation pupil to generate a red reflex in the first, third and fourth observation pupil, and a main illumination in the second observation pupil, the main illumination having a larger field of illumination than the coaxial illumination. The invention also relates to a microscope comprising such an illumination and observation system.

Furthermore, the invention relates to a microscopying method for illuminating and observing an object by four observation pupils, the method comprising illuminating the object with coaxial illumination through three of the four observation pupils and providing a main illumination in the remaining observation pupil, the main illumination generating a larger field of illumination than the coaxial illumination in any of the three observation pupils.

BACKGROUND OF THE INVENTION

Ophthalmic microscopes, i.e. microscopes that are used for eye surgery, comprise typically two different kinds of illumination. A first illumination serves to illuminate a rather large field of view in the observed object, i.e. the eye to be operated. This illumination lightens the surroundings of the area, where the actual observation takes place. At the observed eye, the illuminated field of this type of illumination has a diameter between 60 mm and 80 mm. This illumination is referred to in the following as a main illumination. In eye surgery, the main illumination is primarily used to visualize outer eye structures like the cornea.

A second type of illumination makes use of the characteristic of the eye's retina to provide a reddish-orange reflection of light called the red reflex. The red reflex offers much higher contrasts than the main illumination and is mainly used for cataract surgery. The red reflex is generated by an illumination, which is coaxial or at least closely coaxial, e.g. within +/−5°, to the axis of an observer's pupil which looks through the illumination and observation system onto the observed eye. A known system for generating a red reflex is, for example, described in EP 0 661 020 B1. The field of illumination of the coaxial illumination is usually much smaller than the diameter of the main illumination, e.g. by a factor 2 to 5.

The image quality of the known illumination and observation systems, although having made large progress in the past, still leaves room for improvement.

SUMMARY OF THE INVENTION

It is therefore the object of the invention to provide an illumination observation system that is easy to operate, inexpensive in its design, and at the same time offers superior observation properties.

According to the invention, this object is solved for the illumination and observation system mentioned at the beginning in that the main illumination overlaps at least 50% with the second observation pupil to generate a red reflex in the second observation pupil.

The object is also solved by a microscope comprising such an illumination and observation system and by the above-mentioned microscopying method for illuminating a reflecting object in that the main illumination overlaps at least 50% of the remaining one of the four observation pupils.

Using this simple concept improves the stereoscopic quality for the observer using the second observation pupil, as due to the overlap of at least 50%, a homogenous red-reflex can be generated by the main illumination in the remaining, second, observation pupil. This red reflex is perceived by the observer together with the red reflex generated by the coaxial illumination in one of the other observation pupils, i.e. first, third or fourth observation pupil. Both red reflexes generate an improved stereoscopic perception.

The solution according to the invention can be further improved by the following features, which can be combined independently of one another.

In order to improve the quality and strength of the red reflex, the main illumination may be coaxial within ±5° to the optical axis of the second observation pupil. In particular, the main illumination may overlap the optical axis of the second observation pupil.

To improve the overall quality of all red reflexes in all of the observation pupils, it is preferred that the coaxial illumination in the first, third and fourth observation pupil overlaps at least 50% with the first, second and third observation pupil.

In particular, the coaxial illumination may overlap the optical axis of at least one of the first, third and fourth observation pupils.

For obtaining a strong red reflex, a separate light source may be associated with each observation pupil. The light sources may in particular be LEDs. It is preferred that the light sources that are associated with the coaxial illumination in the first, third and fourth observation pupil are arranged in a pattern that mirrors the geometric arrangement of these observation pupils. For example, the LEDs providing the coaxial illumination in the first, third and fourth observation pupil may arrange in a triangular pattern which matches the triangular pattern of the arrangement of the associated first, third and fourth observation pupil.

In operation of the illumination and observation system or of the microscope, the intensity of the coaxial illumination in at least one of the first, third and fourth observation pupil may be adjusted to provide a subjectively optimum red reflex for the respective observer. The intensities may be adjusted individually or coupled together. In order to maintain the stereoscopic quality of the red reflex for the observer using the second observation pupil, it is of advantage if the intensity of the main illumination is coupled to the intensity of the coaxial illumination in at least one of the first, third and fourth observation pupil. In particular, a control subsystem may be provided, which is adapted to control the intensity of the main illumination in the second observation pupil to follow the intensity of the coaxial illumination in at least one of the first, third and fourth observation pupil.

The control subsystem may be adapted to automatically change the intensity of the main illumination in the second observation pupil depending on a change in the intensity of the coaxial illumination in at least one of the first, third and fourth observation pupil. The dependency may be constant, i.e. the ratio of the intensity of the main illumination to the coaxial illumination in at least one of the first, third and fourth observation pupil is maintained constant at a target ratio independent of the current intensity. In a more complex variant, the control subsystem may be adapted to maintain a linear or non-linear characteristic between the intensity of the main illumination and the intensity of the coaxial illumination in at least one of the first, third and fourth observation pupil.

According to another embodiment, a manipulator subsystem may be provided which is adapted to allow manual adjusting of the intensity of the coaxial illumination in at least one of the first, third and fourth observation pupil. The intensities of the coaxial illumination in the first, third and fourth illumination may be coupled to each other.

It is preferred that an adjustment is only possible for the coaxial illumination of one observer, in particular a surgeon, which uses the third and fourth observation pupil. Due to the coupling of the coaxial illumination to each other, an adjustment of the intensity of the coaxial illumination in the third and fourth observation pupil automatically leads to a corresponding change of the intensity of the coaxial illumination in the first observation pupil. For repair or maintenance purposes, e.g. to calibrate the separate light sources for the first, third and fourth observation pupil, the coaxial illumination in these observation pupils may also be decoupled from each other.

The manipulator subsystem may, in a further embodiment, be adapted to switch the illumination and observation system upon operation from a coupled state, in which the intensity of the main illumination and the second observation pupil is coupled to the intensity of the coaxial illumination in at least one of the first, third and fourth observation pupil, to a decoupled state, in which the intensity of the main illumination in the second observation pupil is decoupled from the intensity of the coaxial illumination in at least one of the first, third and fourth observation pupil. This allows adjusting the relative intensity of the main illumination to the intensity of the red reflex for the observer who uses two of the first, third and fourth observation pupil and thus relies solely on the coaxial illumination to provide the red reflex. The adjustment will typically be the surgeon.

The manipulator subsystem may be adapted to store the relative intensity of the main illumination to the coaxial illumination if the manipulator subsystem is switched from the decoupled state to the coupled state. The control subsystem then may use this new ratio as target ratio which is to be maintained in the automatic adjustment of the intensity of the main illumination in the second observation pupil.

A memory subsystem may be provided, in which the target ratio or a linear or non-linear characteristic is stored. The manipulator subsystem may also be adapted to allow a direct adjustment of the target ratio by providing mechanical and/or software-implemented manipulators which, if operated by a user, affect the target ratio or characteristic.

For adjustment of the various parameters, the manipulator subsystem may comprise adjustment knobs or sliders or virtual adjustment knobs and sliders on a computer screen.

BRIEF DESCRIPTION OF THE DRAWING VIEWS

In the following, the invention is explained exemplarily with reference to the drawings. In the drawings, the same reference numerals are used for elements that correspond to each other. The various features in the drawings can be combined independently of each other as is laid out above.

In the drawings:

FIG. 3A shows a schematic representation of a red reflex resulting from an illumination and observation system as shown in FIG. 3B;

FIG. 3B shows a schematic representation of the illumination generating the red reflex of FIG. 3A;

FIG. 4A shows a schematic representation of a red reflex resulting from an illumination and observation system as shown in FIG. 4B;

FIG. 4B shows a schematic representation of the illumination generating the red reflex of FIG. 4A;

FIG. 5A shows a schematic representation of a red reflex resulting from an illumination as shown in FIG. 5B;

FIG. 5B shows a schematic representation of the illumination generating the red reflex of FIG. 5A;

DETAILED DESCRIPTION OF THE INVENTION

Figure 1:
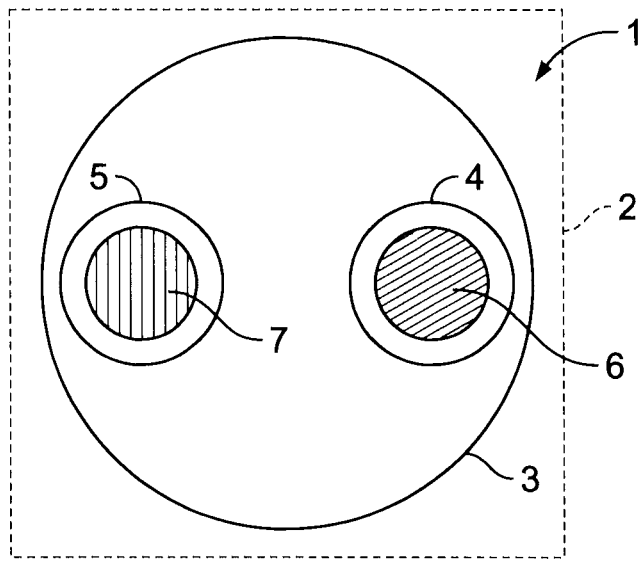
FIG. 1 shows a schematic representation of an illumination and observation system according to the invention.
Figure 2:
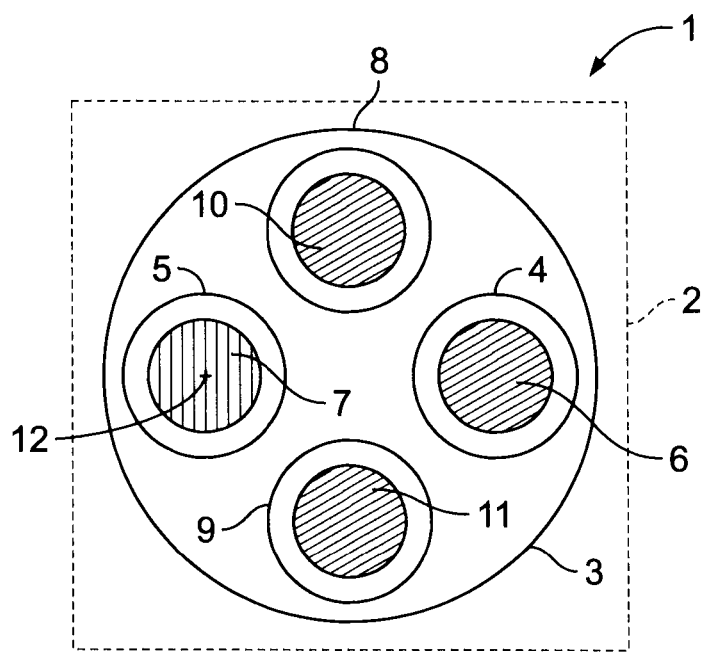
FIG. 2 shows a schematic representation of the illumination and observation system according to FIG. 1 with additional components.

First, the design and function of an illumination and observation system 1 in a microscope 2 is explained with reference to FIG. 1. FIG. 1 shows a schematic plan view of a main objective lens 3 with a first observation pupil 4 and a second observation pupil 5. The first observation pupil 4 and the second observation pupil 5 are preferably for an assistant or a student assisting in e.g. eye surgery.

A coaxial illumination 6 is directed through the first observation pupil 4, whereas a main illumination 7 is directed through the second observation pupil 5. Preferably, there is no overlap of the main illumination with the first observation pupil 4 and/or there is no coaxial illumination in the second observation pupil 5.

The set up shown in FIG. 1 is particularly useful for microscopes 2 which are used in eye surgery, i.e. so-called ophthalmic microscopes. At the observed object, i.e. in the object plane, in such a case the eye to be operated upon, the main illumination 7 generates a field of illumination which has a larger diameter in the observation plane than the coaxial illumination 6. The field of illumination may be between 60 mm and 80 mm. The axis of the coaxial illumination 6 deviates only slightly from the optical axis of the first observation pupil 4, e.g. by less than +/−5°.

As can be seen in FIG. 1, the main illumination 7 is also arranged to be coaxial at least within +/−5° to the optical axis of the second observation pupil 5. Thus, both the main illumination 7 and the coaxial illumination 6 are able to generate a red reflex during eye surgery.

To provide a homogeneous red reflex, it is preferred that the main illumination 7 and the coaxial illumination 6 overlap the respective observation pupil 5, 4 at least by 50% with regard to its area.

To provide a good stereoscopic effect in the red reflex, the intensity of the main illumination should be kept at a certain target ratio to the intensity of the coaxial illumination. A preferred intensity target ratio is in a range of 0.2 to 5, particularly preferable in a range of 0.5 to 2, even more preferable in a range of 0.5 to 1.5 measured in lux. Thereby, the intensity of the red reflex in the first observation pupil is perceived to be identical or almost identical to the intensity of the red reflex in the second observation pupil.

The target ratio of the intensity of the main illumination to the coaxial illumination is maintained by the illumination and observation system 1 independently of the intensity of the coaxial illumination 6. In particular, the intensity of the main illumination 7 may be coupled to the intensity of the coaxial illumination 6: if the intensity of the coaxial illumination 6 changes, e.g. by manual operation of a user, the intensity of the main illumination 7 follows to maintain the same intensity ratio of the red reflex in both observation pupils 4, 5.

The observation illumination system shown in FIG. 1 may be expanded to comprise a third observation pupil 8 and a fourth observation pupil 9, each of which is provided with a respective coaxial illumination 10, 11, which may substantially correspond to the coaxial illumination of the first observation pupil 4.

The third and fourth observation pupil 8, 9 may be specifically used by a surgeon. The coaxial illuminations 10, 11 are preferably identical, comprising identical and/or identically arranged optical elements, to produce an identical red reflex in the observed eye for both observation pupils 8, 9. Preferably, there is no main illumination overlap in the third and/or fourth observation pupil 8, 9.

The intensity of the coaxial illumination 6 for the first observation pupil 4 may be coupled to the intensity of at least one of the coaxial illumination 10 in the third observation pupil 8 and the coaxial illumination 11 in the fourth observation pupil 9. If the surgeon adjusts the intensity of the coaxial illumination 10, 11, the intensity of the coaxial illumination 6 in the first observation pupil 4 will automatically follow. Due to the coupling of the main illumination 7 in the second observation pupil 5 to the intensity of the coaxial illumination 6 in the first observation pupil 4, the intensity of the main illumination 7 will thus automatically follow any adjustment of the coaxial illumination 10, 11 in the third and fourth observation pupil 8, 9.

The coaxial illumination 10 overlaps the third observation pupil 8 by more than 50% and the coaxial illumination 11 overlaps the fourth observation pupil 9 by more than 50%. Moreover, a red reflex is generated in all four observation pupils 4, 5, 8, 9. According to the invention, due to a coaxial alignment of the main illumination, a strong red reflex can be generated in the second observation pupil 5 without the need to install an expensive coaxial illumination. Rather, the main illumination 7 is aligned with the optical axis 12 of the second observation pupil 5 and its intensity is maintained at the target ratio to the intensity of the coaxial illumination in the first observation pupil 4.

Using an overlap of more than 50% increases the homogeneity of the red reflex. This is schematically shown in FIGS. 3A,B, 4A,B and 5A,B. In these figures, a coaxial illumination 6, 10, 11 is shown to overlap with one of the observation pupils 4, 8, 9. The overlap leads to a red reflex which has a perceptible inhomogeneous intensity distribution in the respective observation pupils 4, 8, 9 as seen by the respective observer. Increasing the overlap reduces the inhomogeneity shown in FIGS. 3A, 4A and 5A.

Figure 6:
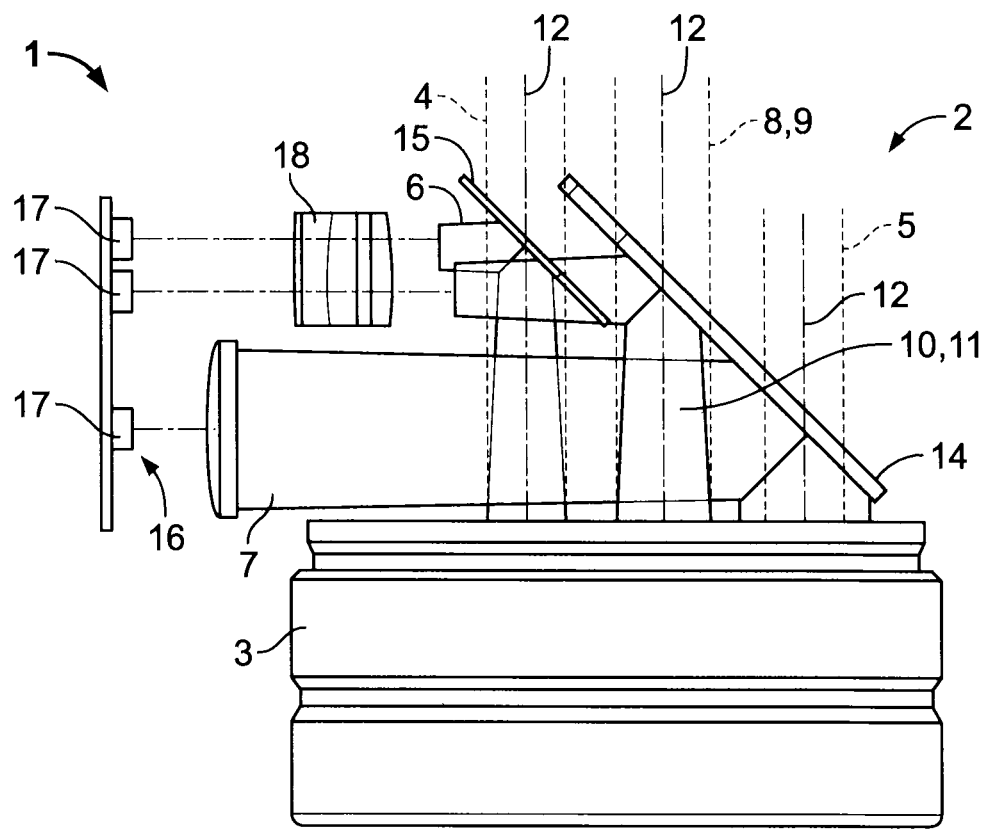
FIG. 6 shows a schematic side view upon the illumination and observation system according to the invention as used in a microscope.

FIG. 6 shows a schematic side view of parts of the illumination and observation system 1 as used in the microscope 2. The illuminations 6, 7, 10, 11 are aligned with and directed through the respective observation pupil 4, 5, 8, 9 by using beam splitters 14, 15. A larger beam splitter 14 is used to deflect the main illumination 7 for the second observation pupil 5 and the coaxial illuminations 10, 11 for the third and fourth observation pupil 8, 9 respectively. A second, smaller beam splitter 15 is used to deflect the coaxial illumination 6 for the first observation pupil 4.

Each of the illuminations 6, 7, 10, 11 is preferably provided with a separate light source 16, which in particular may be an LED 17. As in the view of FIG. 6, the third and fourth observation pupil 8, 9 together with the respective coaxial illuminations 10, 11 are located right behind each other, only one light source 16 is shown for these two coaxial illuminations 10, 11.

Using the beam splitters 14, 15 results in a very good alignment, not only of the coaxial illuminations 6, 10, 11 with the optical axes 12 of the first, third and fourth observation pupil 4, 8, 9, but also of the main illumination 7 with the optical axis 12 of the second observation pupil 5.

Between the light sources 16 and the beam splitters 14, 15, optical elements such as lenses 18 for the coaxial illumination 6, 10, 11 and 19 for the main illumination 7 may be arranged. The optical elements 18, 19 may also comprise an aperture which may be adjustable.

Figure 7:
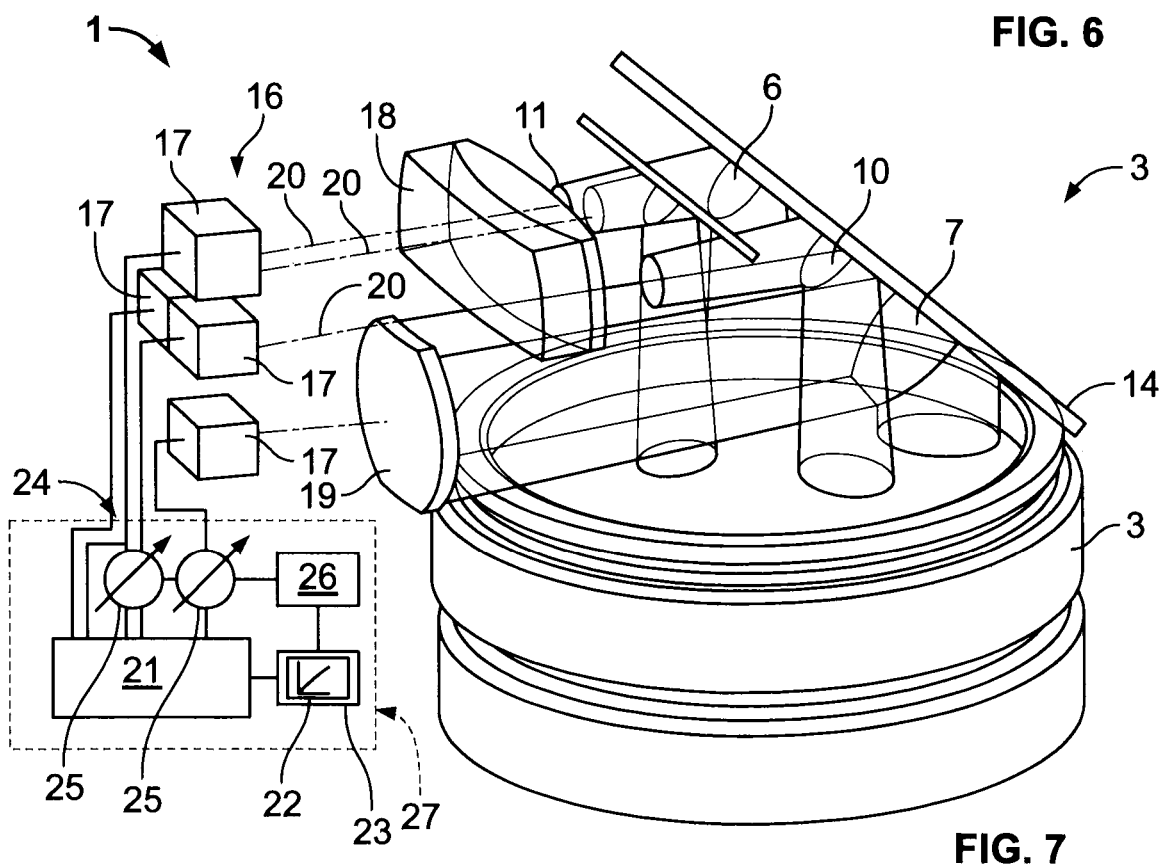
FIG. 7 shows a schematic perspective view of the embodiment shown in FIG. 6 with additional elements.

In FIG. 7, the embodiment of FIG. 6 is shown in a schematic perspective view. From this, it can be seen that there is a single optical element 18 such as a lens associated with the three separate light sources 17 for the coaxial illuminations 6, 10, 11. The illumination and observation system 1 may have an identical design along the illumination paths 20 of the coaxial illuminations 6, 10, 11, so that the coaxial illuminations 6, 10, 11 in the first, third and observation pupil 4, 8, 9 have identical or at least almost identical properties.

The light sources 16 may be arranged geometrically in a pattern that corresponds to the pattern of the observation pupils 4, 8, 9 which are equipped with coaxial illumination 6, 10, 11.

The light sources 16 for generating the coaxial illumination 7, 10, 11 may be adapted to be controlled independently of each other or they may be coupled to each other. A control subsystem 21 is adapted to control the intensity of the light sources 16 for the coaxial illumination 6, 10, 11. The control subsystem 21 may be adapted to couple the coaxial illumination of the third and fourth observation pupil 8, 9 to the coaxial illumination 6 of the first observation pupil 4 and the main illumination 7 of the second observation pupil 5. The coupling can be implemented in the control subsystem 21 using a non-linear or linear coupling characteristic 22. The characteristic 22 can further be implemented by using a simple constant in the form of a target ratio.

A linear or non-linear coupling characteristic may be used to adapt intensity changes better to any intensity-dependent characteristic of perception in the observer's eyes. The coupling can be implemented mechanically, e.g. by mechanically transmitting a motion from one manipulator to another via gears. The coupling can also be implemented electrically by using analog electric components such as amplifiers, resistor networks and capacities to arrive at the desired dependency of the main illumination 7 from at least one of the coaxial illuminations 6, 10, 11. If the coupling is implemented digitally, a digital control may be used, wherein the coupling characteristic 22 may be, e.g. stored as a look-up table.

The coupling characteristic 22 may be stored in a memory subsystem 23, which may comprise mechanical, electric, analog and/or digital components. In its simplest form, the coupling characteristic 22 is just a target ratio of the main illumination 7 to at least one of the coaxial illuminations 6, 10 and/or 11 which is maintained by the control subsystem 21 if the intensity in one of the coaxial illumination 6, 10, 11 changes.

A change in the intensity may be effected by operation of a manipulator subsystem 24. Again, the manipulator subsystem 24 may comprise manually operable manipulators such as adjustment knobs or sliders, and/or electric elements such as adjustable resistors, gates or logical circuits in order to change the intensity of at least one, preferably each of the light sources 16. The manipulator subsystem 24 may also comprise software-implemented manipulators such as virtual sliders or adjustment knobs which are displayed on a computer screen for interaction with a user.

In FIG. 7, two manipulator elements 25 are shown just by way of example. One of the manipulator elements 25 can be activated to control the intensity of the light source 16 of the main illumination 7. The other manipulator element 25 serves to adjust commonly the intensity of all three light sources 16 for the coaxial illuminations 6, 10, 11.

A switch 26 may be provided as part of the manipulator subsystem 24 to activate a subset of the manipulator elements 25 and/or to switch the illumination and observation system 1 from a coupled state, in which the main illumination 7 is coupled to at least one of the coaxial illumination 6, 10 and 11, to a decoupled state, in which this coupling is released and the intensities of these illuminations can be adjusted independently. It is preferred that upon switching from a decoupled to the coupled state, the newly obtained ratio between the intensity of the illumination in one of the coaxial illuminations 6, 10, 11 is stored in the memory subsystem 23 as the new target ratio.

This allows for example that the surgeon adjusts the relative intensity of the main illumination 7 to the coaxial illumination 10, 11 to a ratio, which for him individually yields the best stereoscopic image. For this adjustment, the switching subsystem 26 is activated and the decoupled state is assumed. Once the surgeon has adapted the relative intensities of the coaxial and the main illumination 10, 11, 7 to his needs, he again activates the switching subsystem 26 in order to commit the new target ratio to the memory subsystem 23 and switch to the coupled state. From now on, any change of the intensity of the coaxial illuminations 6, 10, 11 automatically triggers a corresponding change in the intensity of the main illumination 7 to maintain the target ratio. This coupling and intensity change is controlled by the control subsystem 21.

Especially for maintenance purposes, it may be desirable that the illumination and observation subsystem 1 can be switched into a decoupled state, in which the intensities of all light sources 16 can be adjusted independently of each other. Once this adjustment is done and the decoupling is switched off to enter the coupled state, the relative intensities of all the light sources 16 may be committed to a storage subsystem.

Although the storage subsystem 23 and the switching subsystem 26 as well as the manipulator subsystem 24 are shown to be separate from the control subsystem 21, all these subsystems may be integrated into a single control unit 27, such as a computer or an ASIC.

REFERENCE NUMERALS 1 illumination and observation system
2 microscope
3 main objective lens
4 first observation pupil
5 second observation pupil
6 coaxial illumination
7 main illumination
8 third observation pupil
9 fourth observation pupil
10 coaxial illumination in third observation pupil
11 coaxial illumination in fourth observation pupil
12 optical axis
13 red reflex
14 beam splitter or deflecting optical element
15 beam splitter or other deflecting optical element
16 light source
17 LED
18 optical elements for coaxial illumination
19 optical elements for main illumination
20 illumination path
21 control subsystem
22 coupling characteristic
23 memory subsystem
24 manipulator subsystem
25 manipulator elements
26 switch
27 control unit

What is claimed is:

1. Illumination and observation system (1) for a microscope (2) for performing eye surgery on an observed eye, the system (1) comprising:
    a main objective lens (3) having a first, second, third and fourth observation pupil (4, 5, 8, 9) for the eyes of two observers,
    a coaxial illumination (6, 10, 11) in the first, third and fourth observation pupil (4, 8, 9) to generate a red reflex (13) in the first, third and fourth observation pupil (4, 8, 9),
    and a main illumination (7), the main illumination (7) having a larger field of illumination than the coaxial illumination,
wherein the main illumination (7) overlaps at least 50% of the second observation pupil (5) to generate a red reflex (13) in the second observation pupil (5), and wherein there is no overlap of the main illumination (7) with the first observation pupil (4) and there is no overlap of the coaxial illumination (6, 10, 11) with the second observation pupil (5).

2. Illumination and observation system (1) according to claim 1, wherein the main illumination (7) is coaxial within ±5° to an optical axis (12) of the second observation pupil (5).

3. Illumination and observation system (1) according to claim 1, wherein the coaxial illumination in the first, third and fourth observation pupil (4, 8, 9) overlaps at least 50% with the first, second and third observation pupil (4, 5, 8).

4. Illumination and observation system (1) according to claim 1, wherein each of the first, second, third and fourth observation pupil (4, 5, 8, 9) is associated with a separate light source (16).

5. Illumination and observation system (1) according to claim 4, wherein each light source (16) comprises at least one light source (17), the light sources (17) at least for the coaxial illumination (6, 10, 11) being arranged in a pattern that mirrors an arrangement of the first, second, third and fourth observation pupil (4, 5, 8, 9).

6. Illumination and observation system (1) according to claim 1, wherein the main illumination (7) is coupled to the coaxial illumination (6, 10, 11) in at least one of the first, third and fourth observation pupil (4, 8, 9).

7. Illumination and observation system (1) according to claim 1, further comprising a control subsystem (21, 27) adapted to automatically change an intensity of the main illumination (7) depending on a change in an intensity of the coaxial illumination (6, 10, 11) in at least one of the first, third and fourth observation pupil (4, 8, 9).

8. Illumination and observation system (1) according to claim 7, further comprising a manipulator subsystem (24) adapted to switch the illumination and observation system (1) upon operation from a coupled state, in which an intensity of the main illumination (7) in the second observation pupil (5) is coupled to an intensity of the coaxial illumination (6, 10, 11) of at least one of the first, third and fourth observation pupil (4, 8, 9), to a decoupled state, in which the intensity of the main illumination (7) is decoupled from the intensity of the coaxial illumination (6, 10, 11).

9. Illumination and observation system (1) according to claim 8, further comprising a memory subsystem (23) in which a target ratio for the coupling of the intensity of the main illumination (7) in the second observation pupil (5) to the intensity of the coaxial illumination (6, 10, 11) in at least one of the first, third and fourth observation pupil (4, 8, 9) is stored.

10. Illumination and observation system (1) according to claim 9, wherein the illumination and observation system (1) is adapted to allow a manual change of the target ratio.

11. Illumination and observation system (1) according to claim 9, wherein the control subsystem (21, 27) is adapted to maintain a ratio of the intensity of the main illumination (7) in the second observation pupil (5) to the intensity of the coaxial illumination (6, 10, 11) in at least one of the first, third and fourth observation pupil (4, 8, 9) at the target ratio.

12. Microscope (2) for eye surgery, wherein the microscope comprises an illumination and observation system (1) according to claim 1.

13. Microscopying method for illuminating and observing an object by first, second, third, and fourth observation pupils (4, 5, 8, 9) of a main objective lens (3), the method comprising:
   illuminating the object with a coaxial illumination (6, 10, 11) through the first, third, and fourth observation pupils (4, 8, 9) and
   providing a main illumination (7) in the second observation pupil (5), the main illumination generating a light field having a larger diameter than the light field of the coaxial illumination (6, 10, 11) in any of the the first, third, fourth observation pupils (4, 8, 9),
wherein the main illumination (7) overlaps the second observation pupil (5) by at least 50%,
wherein there is no overlap of the main illumination (7) with the first observation pupil (4) and there is no overlap of the coaxial illumination (6, 10, 11) with the second observation pupil (5).

14. Illumination and observation system (1) for a microscope (2) for performing eye surgery on an observed eye, the system (1) comprising:
   a first, second, third and fourth observation pupil (4, 5, 8, 9) for the eyes of two observers,
   a coaxial illumination (6, 10, 11) in the first, third and fourth observation pupil (4, 8, 9) to generate a red reflex (13) in the first, third and fourth observation pupil (4, 8, 9),
   and a main illumination (7), the main illumination (7) having a larger field of illumination than the coaxial illumination,
wherein the main illumination (7) overlaps at least 50% of the second observation pupil (5) to generate a red reflex (13) in the second observation pupil (5), and wherein the main illumination (7) is coaxial within ±5° to an optical axis (12) of the second observation pupil (5).

\* \* \* \* \*